(12) United States Patent
Mizuochi

(10) Patent No.: US 7,832,865 B2
(45) Date of Patent: Nov. 16, 2010

(54) OPHTHALMIC PHOTOGRAPHIC APPARATUS

(75) Inventor: Masaharu Mizuochi, Hamamatsu (JP)

(73) Assignee: Kowa Company Ltd. (JP)

( * ) Notice: Subject to any disclaimer, the term of this patent is extended or adjusted under 35 U.S.C. 154(b) by 0 days.

(21) Appl. No.: 12/660,735

(22) Filed: Mar. 3, 2010

(65) Prior Publication Data

US 2010/0165292 A1 Jul. 1, 2010

Related U.S. Application Data

(62) Division of application No. 11/397,468, filed on Apr. 4, 2006, now Pat. No. 7,735,999.

(30) Foreign Application Priority Data

Jun. 14, 2005 (JP) ............................. 2005-173083

(51) Int. Cl.
*A61B 3/14* (2006.01)
*A61B 3/00* (2006.01)

(52) U.S. Cl. ...................................... 351/206; 351/200

(58) Field of Classification Search ................. 351/200, 351/206, 213, 216, 221, 222; 396/215, 264, 396/472
See application file for complete search history.

(56) References Cited

U.S. PATENT DOCUMENTS

| 7,429,107 | B2 * | 9/2008 | Mizuochi | 351/206 |
| 7,735,999 | B2 * | 6/2010 | Mizuochi | 351/206 |

* cited by examiner

*Primary Examiner*—Jack Dinh
(74) *Attorney, Agent, or Firm*—Adams & Wilks

(57) ABSTRACT

A timer function hold mode in which the timer continues the timing function is set in a mydriatic fluorescence mode by operating a timer switch for at least a fixed time, or by simultaneously operating a fluorescence filter switch and the timer switch. If the timer function hold mode is set in the mydriatic fluorescence mode, then the timing of the timer is continued even after the photography mode switches to another photography mode e.g. non-mydriatic or mydriatic color mode. When, on the other hand, the timer function hold mode is not set in the mydriatic fluorescence mode, the timer is caused to be stopped or reset when the mode is switched to the non-mydriatic or mydriatic color mode.

4 Claims, 9 Drawing Sheets

FIG. 2

| Ring Slit | Exciter | Barrier | Photography Mode | Timer Operation /Display | Observing Means | Photographing Means |
|---|---|---|---|---|---|---|
| Standard 11 | No | No | Mydriatic | Disabled/No | Finder or Infrared CCD | (Still Images) Color CCD or 35mm |
| | FA | FA | FA | Enabled | Finder or Infrared CCD | ✕ |
| | IA | No | IA | Enabled | Infrared CCD | |
| Small Pupil 12 | No | No | Non-Mydriatic | Disabled/No | Infrared CCD | (Still Images) Color CCD or 35mm |
| | FA | FA | FA | Disabled/No | Finder or Infrared CCD | |
| | IA | IA | IA | Enabled | Finder or Infrared CCD | (Still Images) Infrared CCD |
| Fluorescence 13 | FA | FA | FA | Enabled | Finder or Infrared CCD | (Still Images) Color CCD or 35mm |

OPHTHALMIC PHOTOGRAPHIC APPARATUS

CROSS-REFERENCE TO RELATED APPLICATIONS

This application is a division of U.S. patent application Ser. No. 11/397,468 filed Apr. 4, 2006, now U.S. Pat. No. 7,735,999 which claims priority of Japanese Patent Application No. 2005-173083 filed Jun. 14, 2005.

BACKGROUND OF THE INVENTION

1. Field of the Invention

The present invention relates to an ophthalmic photographic apparatus having a plurality of photography modes and timing means for measuring the elapsed time since its start by a user command.

2. Description of the Prior Art

There are ophthalmic photographic apparatuses, such as a fundus camera, that are provided with a timer, which is started and stopped in accordance with the operation of a user (examiner), and which is capable of imprinting the time measured by this timer onto the taken image and storing such as electronic data. Such a timer is used, for example, in fluorescence photography to measure and record the elapsed time since a fluorescent agent was intravenously injected.

Meanwhile, an ophthalmic photographic apparatus is known that has a plurality of photography modes such as a mydriatic photography mode wherein a mydriatic agent is dropped into the eye to be examined; a non-mydriatic photography mode wherein the fundus is irradiated with infrared light for observation and photography without a mydriatic agent; a visible light-excited fluorescence photography (also designated as fluorescein angiography; FA) mode for taking a visible light-excited fluorescence image;

and an infrared light-excited fluorescence photography (also designated as indocyanine green angiography; IA) mode for taking an infrared light-excited fluorescence image. It is known to constitute the ophthalmic photographic apparatus so that it is provided with a plurality of timers for the purpose of, for example, independently timing the plurality of modes, as is known from Japanese patent laid open publication No. 322800/96.

There are various problems with the relationship among the plurality of photography modes discussed earlier when managing a timer in an ophthalmic photographic apparatus. For example, there is the case wherein a timer has been started in a certain photography mode and is then temporarily switched to another photography mode. In such a case, various technical concepts can be considered for handling the started timer.

First, it is conceivable that, for example, the timer can be started and stopped only in a specific photography mode. With such a constitution, the timer can be used only in the required photography mode, and it therefore has merits in that the action of the timer is clear, the operation system is simple, and misoperation can be prevented. It is also conceivable that the timer is automatically stopped or reset upon transition to another photography mode, thereby enabling to omit the operation of explicitly stopping the timer.

On the other hand, there is a case wherein the timer is started in a fluorescence photography mode and this mode is switched temporarily to another photography mode. When returning again to the fluorescence photography mode, the user wants to perform fluorescence photography using the time measured by the timer that was previously started. However, it is not possible to meet the demand of such a user with a constitution that automatically stops and resets the timer when switching to another mode.

If, in such a case, a constitution having no automatic stop and reset mechanism is used, the user must always stop the timer if he or she started it. This causes inconvenience during normal usage.

With a system provided with a plurality of timers, as described previously, the operator can separately use those timers in accordance with the photography mode, thus solving the abovementioned deficiency to a certain extent. However, there are other problems, such as the increased complexity and cost of the apparatus due to the provision of a plurality of timers and independent displaying means, which make the operation confusing and difficult to understand, and the user will inadvertently view a timer display other than the one intended.

Although a timer function hold mode can be provided to solve such troubles, there is a problem in that the photographing operation procedure is complicated. For example, the mydriatic fluorescence photography is initiated with the timer function hold mode, and the mydriatic color mode is then performed. The original mydriatic fluorescence mode must be manually restored.

Particularly in the case of fluorescence photography, the work of the examiner or the operation procedure is complex even under normal circumstances, which increases the burden on the examiner. Accordingly, there is a strong demand for an ophthalmic photographic apparatus that is easy to operate.

It is therefore an object of the present invention to provide an ophthalmic photographic apparatus that can be constituted simply and at low cost, has a simple operation system, and can maintain the timing information of the timer as needed even while switching among a plurality of photography modes.

SUMMARY OF THE INVENTION

According to the present invention, an ophthalmic photographic apparatus has a plurality of photography modes and a timing means for measuring the elapsed time since its start by the command of a user. The apparatus comprises a timer function holing means responsive to a prescribed timer function hold operation in a first photography mode to set a timer function hold mode. When the timer function hold mode is set in the first photography mode, the timing means continues measuring the time even after the mode is switched therefrom to a second photography mode, and when the timer function hold mode is not set in the first photography mode, the timing means is caused to be stopped or reset when the mode is switched to the second photography mode.

According to another embodiment, when the timer function hold mode is set in the first photography mode, the timing means continues measuring the time even after the mode is switched therefrom to a second photography mode, and the first photography mode is restored automatically after a prescribed number of images is taken in the second photography mode, or restored automatically after a prescribed time is elapsed after the mode is switched to the second photography mode.

The present invention can provide a simple, low-cost and easy-to-operate ophthalmic photographic apparatus because the timing information of the timer can be maintained as needed even while switching among a plurality of photography modes, and can automatically return to the original photography mode without the need to perform superfluous operations.

Further features of the invention, its nature and various advantages will be more apparent from the accompanying drawings and following detailed description of the invention.

BRIEF DESCRIPTION OF THE DRAWINGS

FIG. 2 is a table showing photography modes of the apparatus in FIG. 1 and elements and devices used in the photography modes.

DESCRIPTION OF THE PREFERRED EMBODIMENT

The invention will now be described with reference to the accompanying drawings.

Figure 1:
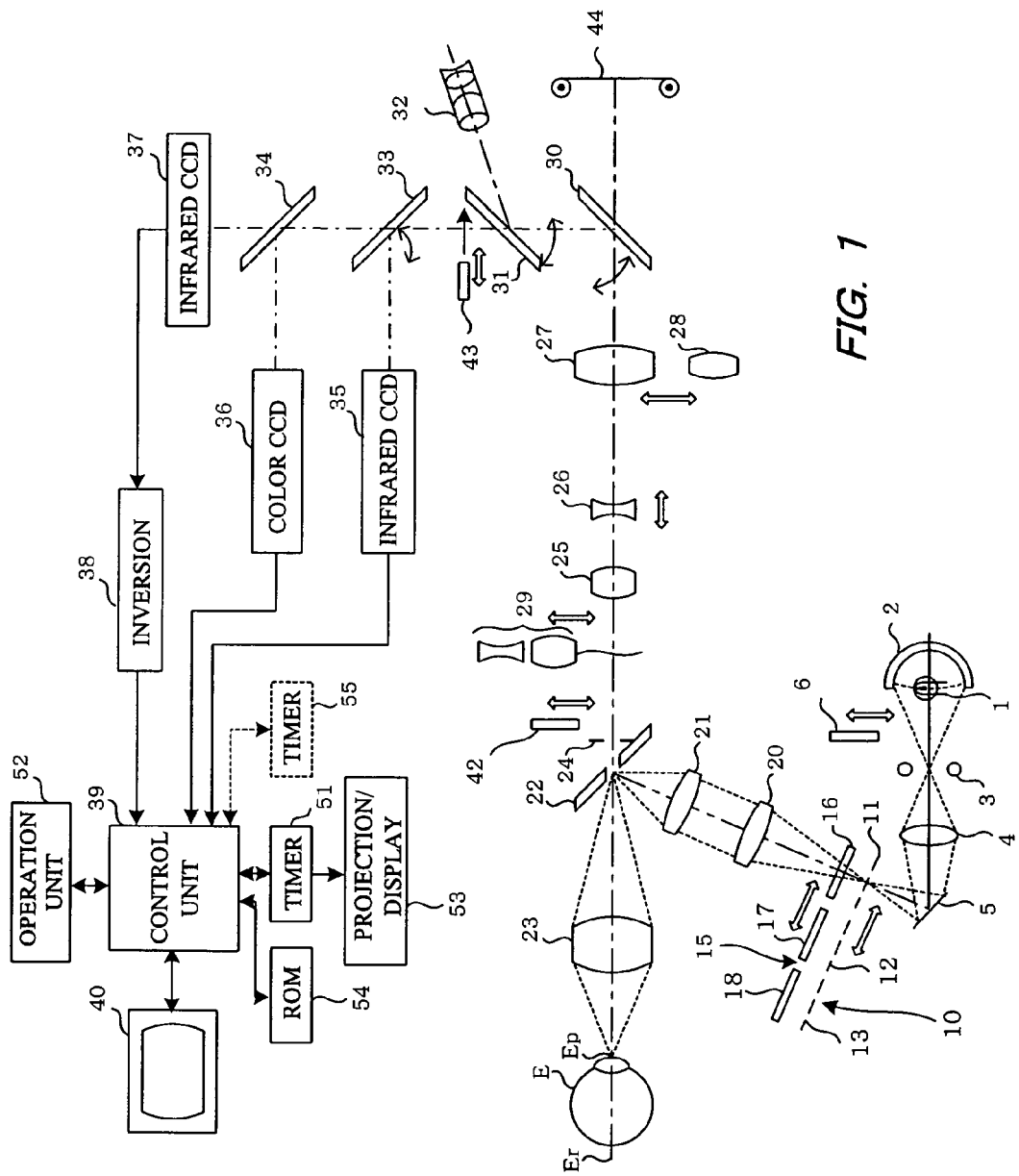
FIG. 1 is an explanatory view showing an ophthalmic photographic apparatus according to the present invention.

FIG. 1 shows a fundus camera that serves as an ophthalmic photographic apparatus according to the present invention. In FIG. 1, a light beam from an observation light source 1, such as a halogen lamp, is condensed by a concave mirror 2, passes through a flash lamp 3 serving as a photographing light source and a condenser lens 4, and is reflected by a mirror 5. The reflected light beam then passes through relay lenses 20, 21, and is reflected by an apertured fully reflecting mirror 22. The light beam reflected by the mirror 22 is then concentrated by an objective 23 at a pupil Ep of a subject eye E and then impinges on the eye fundus Er thereof.

In the non-mydriatic mode, an infrared light transmitting filter 6 is inserted in the rear of the observation light source 1 in the optical path of the illumination optical system. The illumination optical system is further provided with a turret disk 10 that can interchange a ring slit among a plurality of ring slits 11 to 13, and a turret disk 15 that can interchange an illumination filter among a plurality of illumination filters 16 to 18.

The turret disk 10 is constituted as a rotary system wherein a standard ring slit (first ring stop) 11, a small-pupil ring slit (second ring stop) 12, and a large fluorescence ring slit (third ring stop) 13 are arrayed at the circumferential portion. The disk is rotated to insert any one of its ring slits into the optical axis of the illumination optical system in such a way that the ring slit center is aligned thereto.

The illumination light passing through the ring shaped slit forms an image at the position of the pupil Ep of the subject eye E to uniformly illuminate the eye fundus thereof. The deleterious reflected light from the fundus is shielded by the image of a circular light shielding plate of each ring slit. The standard ring slit 11 is the ring slit normally used, and the small-pupil ring slit 12 is used when the non-mydriatic photography is performed, when the mydriatic state of the examinee is insufficient, or when the examinee is a child. Accordingly, the outer diameter of the small-pupil ring slit 12 is made smaller than the standard ring slit, and its inner diameter is also reduced to prevent a reduction in the amount of illumination light. The fluorescence ring slit 13 is used principally during infrared light-excited fluorescence photography. The outer diameter of the ring slit 13 is therefore larger than that of the standard ring slit 11 with its inner diameter reduced so that a large amount of illumination light impinges on the pupil Ep of the subject eye E. The normal standard ring slit 11 is used during visible light-excited fluorescence photography and the large fluorescence ring slit 13 can be used if a large amount of light is required.

The turret disk 15 includes a passthrough filter 16 for transmitting all of the light beam, an exciter filter 17 for visible light-excited fluorescence that transmits blue light in the range of 450 to 520 nm, and an exciter filter 18 for infrared light-excited fluorescence that transmits infrared light in the range of 700 to 800 nm. Any illumination light filter can be inserted in the optical path of the illumination optical system by rotating the turret disk 15. The passthrough filter 16 is inserted in the optical path to transmit all of the light beam. The exciter filter 17 is inserted in the optical path during visible light-excited fluorescence photography, and the exciter filter 18 is inserted in the optical path during infrared light-excited fluorescence photography to transmit only light in the infrared region.

The reflected light from the eye fundus Er of the subject eye E once again passes through the center part of the pupil Ep, is received via the objective 23, and passes through the aperture of the fully reflecting mirror 22. The light beam then passes through a photographic stop 24, focusing lenses 25, 26, and an image forming lens 27 arranged in the optical path of the photographic optical system, and impinges on a return mirror 30 (first return mirror). The image forming lens 27 can be exchanged with an image forming lens 28, which has a different magnification, thereby constituting a variable magnification mechanism. During visible light-excited fluorescence photography, a barrier filter 42 can be inserted in the photographing optical path between the photographic stop 24 and the focusing lens 25 in order to transmit the visible light-excited fluorescence from the fundus.

Diopter compensating lenses 29 comprise a plurality of lenses having differing diopter compensation powers for compensating the diopter of the subject eye E, and the diopter compensating lens selected using an operation panel (FIG. 4 and FIG. 7) is inserted between the photographing stop 24 and the focusing lens 25.

The light beam from the fundus, which was reflected by the return mirror 30, is reflected by a return mirror 31 (second return mirror) and then enters an eyepiece (viewfinder) 32, which constitutes a naked eye observation optical system, and the examiner can therefore observe the fundus image. If the infrared light transmitting filter 6 is inserted and the return mirror 31 flips up so that it retracts from the optical path, then the light beam from the fundus is reflected by a return mirror 33 (third return mirror) and enters an infrared light observation optical system. This infrared light observation optical system comprises an infrared CCD (infrared light electronic imaging device) 35 that is sensitive to infrared light, and the infrared fundus image taken thereby is displayed on a monitor 40 via a control unit 39. Because the imaging device 35 takes an image during observation of the fundus, an infrared moving image of the fundus taken during that time is displayed on the monitor 40, and it is therefore possible to perform alignment and focusing while the examiner observes the fundus image on the monitor 40.

In addition, an infrared light-excited fluorescence barrier filter 43, which transmits infrared light in the range of 820 to 900 nm during infrared light-excited fluorescence photography, can be inserted in the optical path between the return mirrors 31 and 33.

When the return mirror 33 retracts from the optical path, the light beam from the eye fundus impinges on a dichroic mirror 34 that separates the beam into visible light and infrared light. The visible light reflected by the dichroic mirror 34 enters a color CCD (visible light electronic imaging device) 36 sensitive to visible light;

meanwhile, the infrared light transmitted through the dichroic mirror 34 enters an infrared CCD (infrared light electronic imaging device) 37 sensitive to infrared light. Because the fundus image taken by the color CCD 36 is an image that was reflected one extra time by the dichroic mirror 34, it is an inverted image of the fundus image taken by the infrared CCD 37. Consequently, an image inverting circuit 38 is provided, which performs image processing so that the image from the infrared CCD 37 is inverted and vertically matches the taken image. Because these imaging devices 36 and 37 take a fundus image obtained by the light emitted from the flash lamp 3, a still image of the fundus is displayed via the control unit 39 on the monitor 40. Although not shown in FIG. 1, a recording apparatus is provided, which can record the fundus images taken by the imaging devices 36 and 37.

When the return mirror 30 retracts from the optical path, the fundus image can be imaged on a photographic film 44, such as 35 mm film. The fundus image can also be taken using an imaging device equivalent to the color CCD 36 instead of this photographic film.

The control unit 39 comprises a microprocessor and the like, and controls the action of the entire apparatus in accordance with a control program stored in a ROM 54. The control unit 39 is connected to a timer 51, as well as an operation unit 52, which comprises a display, operation switches, and the like.

The timer 51 is a single timer element that, for example, frequency divides the system clock at a prescribed frequency division ratio in order to measure the elapsed time since the timer was started. The timing information is displayed on a display of the operation unit 52 under control of a projection and display control circuit 53, and is imprinted in the taken (observed) image using a projection circuit, a superimposing circuit, and the like, or recorded in a data file associated with the taken image. If visual/infrared light-excited fluorescence modes are selected as discussed later, then a timer 55 can be provided that is capable of running separately from the timer 51.

Figure 3:
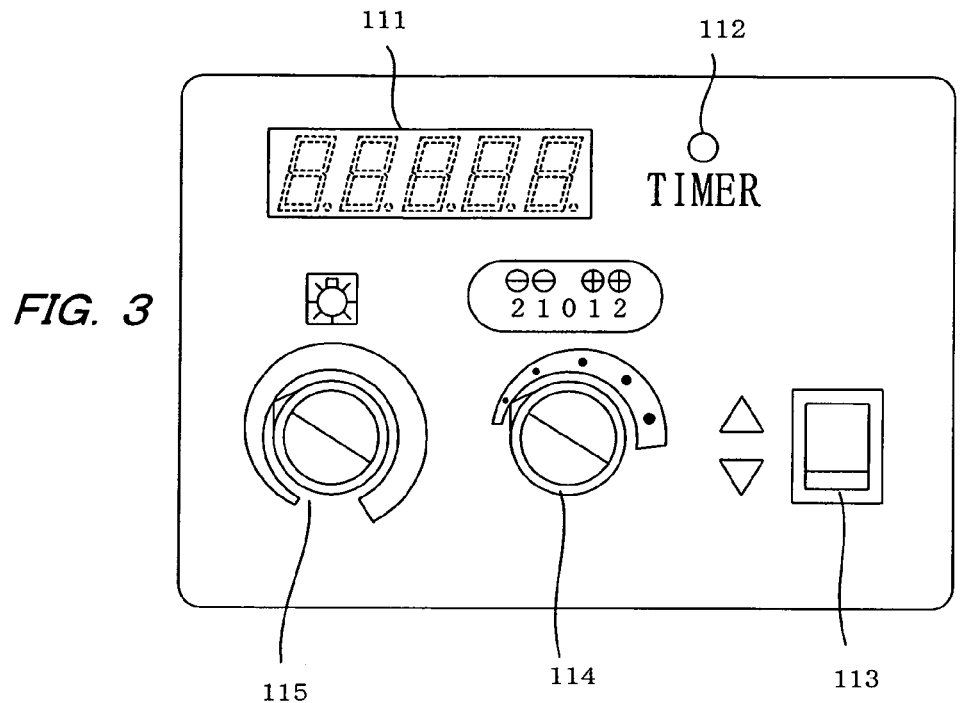
FIG. 3 is an explanatory view showing the operation panel of the apparatus of FIG. 1.
Figure 4:
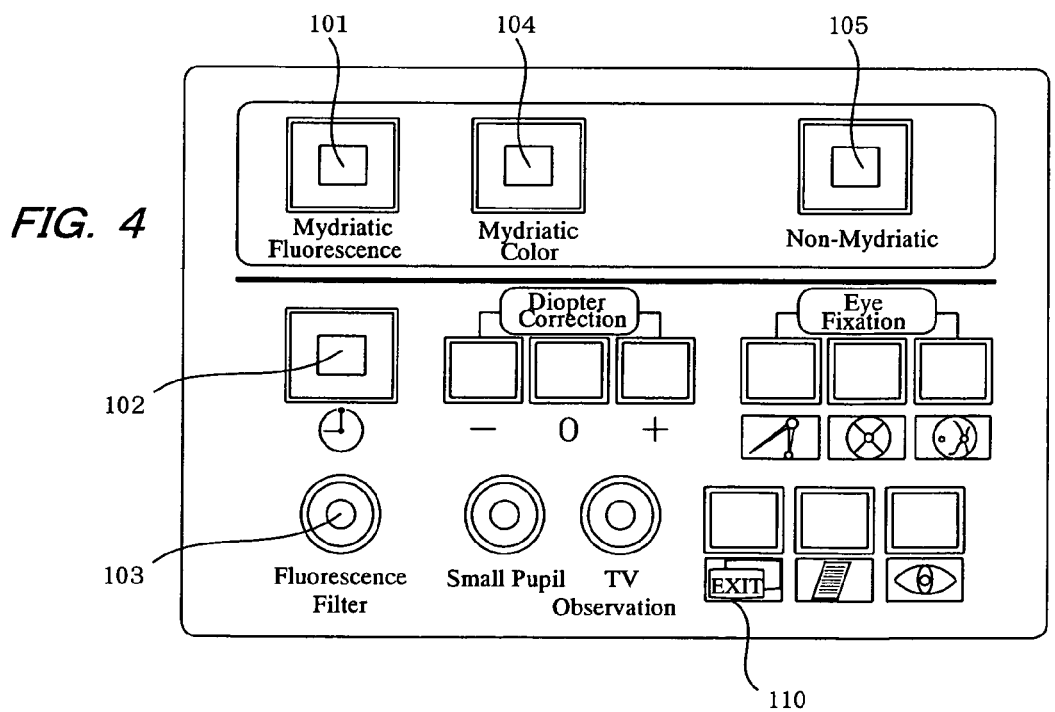
FIG. 4 is an explanatory view showing anther panel of the apparatus of FIG. 1.

The operation unit 52 is used to control the overall imaging function and the observation by the user (examiner). FIG. 3 and FIG. 4 show the operation panel in the operation unit 52. To simplify the explanation of the present embodiment, the operation panels are shown in FIG. 3 and FIG. 4 as being seperated, but it can of course be integrated in a single operation panel.

The operation panel in FIG. 3 comprises a time display unit 111, which includes display elements, such as LCDs and LEDs, that display the timing information of the timer 51 in FIG. 1; an LED 112 constituted so that it displays the timer control (the state of the timer function hold mode, and the like), which is discussed later; a camera changeover switch 113; an exposure adjustment dial 114; and an observation light quantity adjustment dial 115. The camera changeover switch 113 is principally for the purpose of switching between a 35 mm film photography system and the systems of the CCDs 35 to 37. For example, when the camera changeover switch 113 is switched to the lower side in the figure, the various types of mirrors are controlled so that an image can be taken on 35 mm film, and, when the camera changeover switch 113 is switched to the upper side in the figure, the various types of mirrors are controlled so that the CCDs 35-37 can be used to take images.

The operation panel in FIG. 4 is provided with a mydriatic fluorescence switch 101 for setting a mydriatic fluorescence mode, a timer switch 102 for timer control, a fluorescence filter switch 103 for fluorescence filter control, a mydriatic color switch 104 for setting a mydriatic color (non-fluorescence) mode, and a non-mydriatic switch 105 for setting the non-mydriatic (fluorescence/non-fluorescence) mode.

The mydriatic fluorescence switch 101 is a switch that sets the mydriatic fluorescence mode. In the present embodiment, the photography mode transitions to the mydriatic fluorescence mode when the mydriatic fluorescence switch 101 is operated, and the exciter filter 17 for visible light-excited fluorescence is simultaneously inserted in the illumination optical system. An example of using the exciter filter 18 for infrared light-excited fluorescence will be described later.

The fluorescence filter switch 103 is for the purpose of controlling the insertion of a fluorescence filter (in particular, a barrier filter). In the present embodiment, if the fluorescence filter switch 103 is operated after the photography mode has entered the mydriatic fluorescence mode by the operation of the mydriatic fluorescence switch 101 as mentioned above, then the barrier filter 42 (visible) or the barrier filter 43 (infrared) is inserted. The fluorescence filter switch 103 may also be used in controlling the timer function hold mode, which is discussed later.

The timer switch 102 is used to start and stop the timer 51 by a prescribed operation system, e.g., a toggle operation. This timer operation is enabled only in specific modes such as fluorescence photography including the non-mydriatic fluorescence photography, visible or infrared light-excited fluorescence photography, and is disabled in other modes.

A switch 110 is an EXIT switch and is used, for example, to cancel a set mode and to return to the setting process from the photographing process when examining another examinee.

Furthermore, it is possible to control the timer function hold mode by an operation that combines the fluorescence filter switch 103 and the timer switch 102, as discussed later.

In addition, the operation panel in FIG. 4 is provided with a switch for selecting the small-pupil ring slit (12), a switch for selecting one of the previously discussed diopter compensating lenses 29 in accordance with the diopter of the eye to be examined, and a switch for operating a fixation lamp (not shown) for, for example, guiding the eye to be examined.

With the ophthalmic photographic apparatus constituted as described above, it is possible to take an image in the various photography modes, such as mydriatic photography, non-mydriatic photography, visible light-excited fluorescence photography, and infrared light-excited fluorescence photography, and normal color photography is performed by mydriatic photography or non-mydriatic photography.

FIG. 2 lists each photography mode, and the combination of the ring slit, the exciter filter, the barrier filter, the observing means, and the photographing means used in the respective photography mode. FIG. 2 distinguishes between the settings for the case of using the small-pupil ring slit 12 and the case of using other ring slits, but there is of course no need for distinction in a product having no small-pupil ring slit. Furthermore, the present applicants have already filed an application in the form of Japanese Patent Application No. 2003-109691, for the technology used to switch a plurality of ring slits, including the miotic ring slit, as shown in FIG. 1 and FIG. 2.

FIG. 2 also lists the timer operation [(ENABLED/DISABLED)] and display (YES/NO) in association with timer control, which is discussed later. With the basic timer control of the present embodiment, the action of the timer is limited only to fluorescence modes, such as visible light-excited fluorescence (FA) or infrared light-excited fluorescence (IA) as listed in FIG. 2. For other modes, control is performed so that operation of the timer switch 102 is disabled, and the timing information of the timer is not displayed (NO) (including the display on the timer display unit 111, the imprinting to the observation optical system, the display on the monitor 40, and the like).

Furthermore, the infrared light-excited fluorescence photography mode of FIG. 2 cannot be directly selected by the user interface in FIG. 4. The control performed in the infrared light-excited fluorescence photography mode is explained later.

Figure 11:
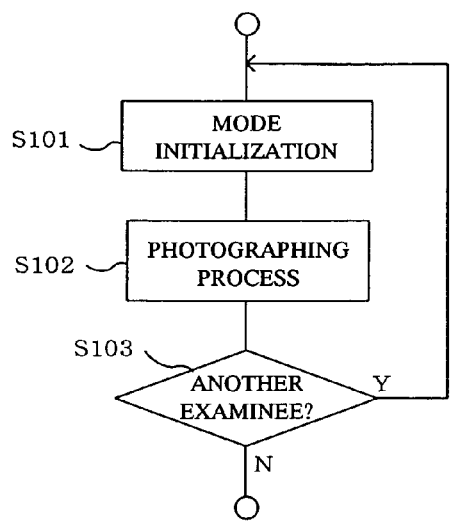
FIG. 11 is a flow chart showing the flow of the entire photographing control of the ophthalmic photographic apparatus.

FIG. 11 shows the flow of function of the entire photographing process of the ophthalmic photographic apparatus of the present invention. If the power supply of the apparatus is turned on or reset, then an initialization process (not shown) is performed, and the flow then proceeds to the photographing process in the sequence shown in FIG. 11.

In step S101 of FIG. 11, a mode initialization process is performed. In this mode initialization process, the photography mode and the detailed settings thereof are cleared.

Thereafter, the actual photographing process is executed in step S102. During the photographing process of step S102, the photography modes, such as mydriatic photography, non-mydriatic photography, visible light-excited fluorescence photography, and infrared light-excited fluorescence photography, can be selected in accordance with the operation of the operation unit 52. Here, the timer function hold mode can also be set by an operation such as the one that will be touched upon later. An example of the photographing process of step S102 will be described in detail, referring to FIG. 5 or FIG. 8.

After the photographing process (step S102), the flow returns to step S101 in accordance with a prescribed setting change operation (e.g., the EXIT switch 110 of the operation unit 52 in FIG. 4 or FIG. 7) in cases such as when examining another examinee in step S103. In this case, in step S101, the photography mode selected by the previous photographing process (step S102) and the detailed settings thereof (including the settings of the timer function hold mode) are temporarily cleared. In step S103, the series of actions is terminated, e.g., by entering a standby mode and the like, if an examinee changeover operation (or a setting change operation) was not performed.

The following explains the operation of the entire optical system in a mydriatic photography (color non-fluorescence) mode as an example. The mydriatic photography mode is set by the operation of the mydriatic color switch 104 in FIG. 4. The operation of the timer 51 by the timer switch 102 is disabled, as indicated in FIG. 2, because fluorescence photography is not performed in this mydriatic color mode.

In the case of the mydriatic photography mode, a mydriatic agent is dropped into the eyes of the examinee. At this time, the infrared light transmitting filter 6 is retracted from the optical path. In this mode, the standard ring slit 11 in the normal case, or the small-pupil ring slit 12 in the small-pupil state, is selected and inserted in the optical path. In addition, the passthrough filter 16 is selected as the illumination filter and is inserted into the optical path. The barrier filters 42, 43 are for fluorescence photography and are therefore retracted from the optical path, and the return mirrors 30, 31, 33 occupy the positions depicted in FIG. 1.

After the light beam from the observation light source 1 is reflected by the mirror 5, it passes through the standard ring slit 11 (or the small-pupil ring slit 12), the passthrough filter 16, and the relay lenses 20, 21, is reflected by the apertured fully reflecting mirror 22, and enters the objective 23 to illuminate the fundus Er. The reflected light from the fundus Er of the subject eye E passes through the objective 23, the apertured fully reflecting mirror 22, the photographic stop 24, the focusing lenses 25, 26, and the image forming lens 27, proceeds via the return mirrors 30, 31, and enters the eyepiece 32. This enables the examiner to observe the fundus by the viewfinder and perform positioning, such as alignment and focusing.

When alignment and focusing are completed, a shutter button (not shown) is operated. In synchronization with this operation, the flash lamp 3 emits light and the return mirror 30 is retracted from the optical path, and it is therefore possible to take a color image of the fundus, such as on the film 44 (or a color CCD). Because it is also possible to observe the fundus by infrared light observation without relying on the eyepiece 32, the infrared light transmitting filter 6 can be inserted at that time, the return mirror 31 is retracted from the optical path, and a moving image of the fundus is taken by the infrared CCD 35. The fundus image is displayed on the monitor 40 via the control unit 39, so that the examiner can observe the fundus via the monitor 40 and can thereby perform alignment and focusing.

Figure 5:
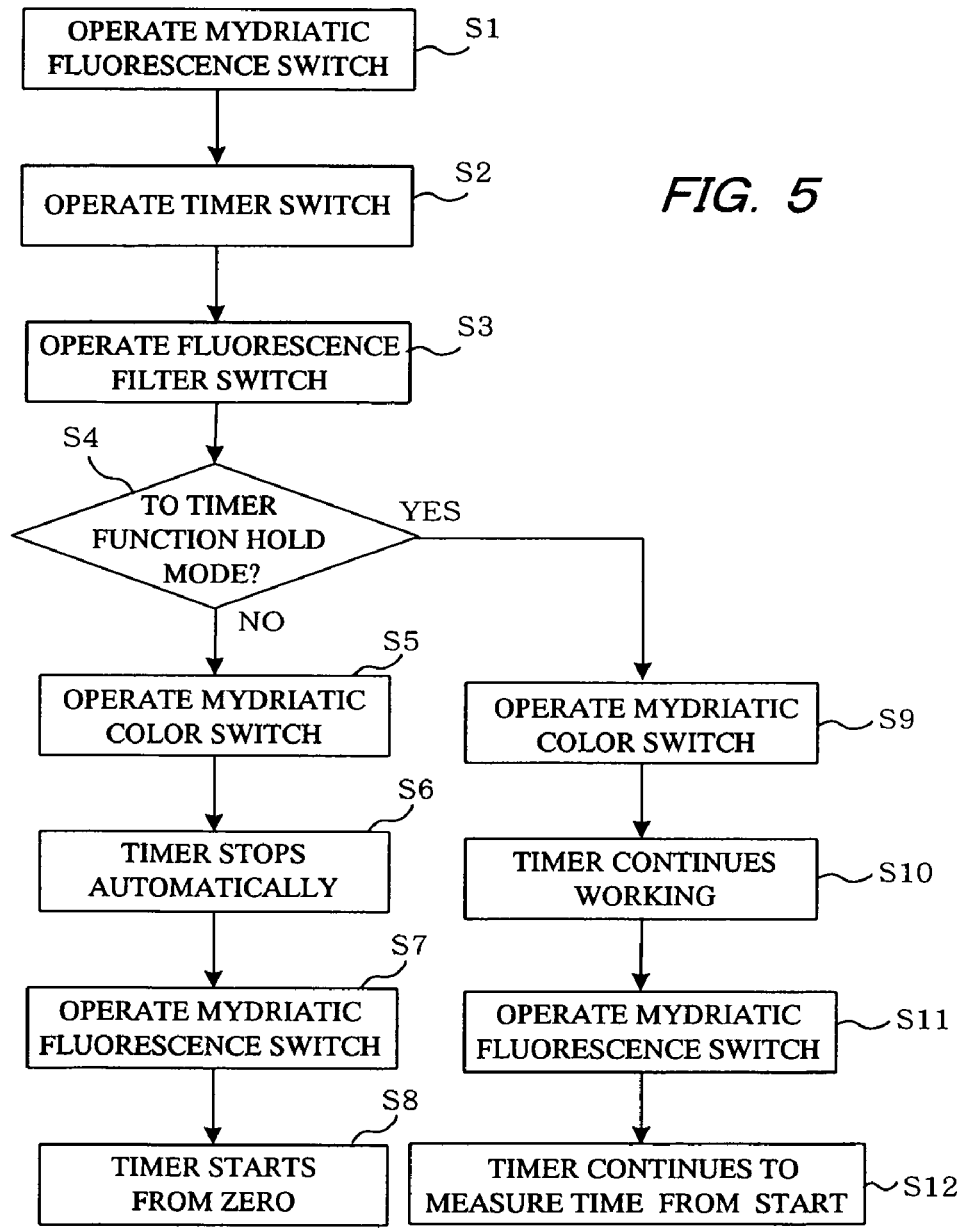
FIG. 5 is a flow chart showing the controls of the timer in the photography modes.

The following explains a mydriatic fluorescence photography mode, including timer control, referencing the user interface in FIG. 4 and the controlling means in FIG. 5. The controlling means in FIG. 5 is stored in advance in the ROM 54 as a control program of the control unit 39.

The normal operation for the mydriatic fluorescence photography mode is to press the mydriatic fluorescence switch 101 in order to enter that mode (step S1). At this time, the exciter filter 17 for visible light-excited fluorescence is inserted in the illumination optical system in response to the depressing of the mydriatic fluorescence switch 101.

Subsequently, a fluorescent agent is intravenously injected into the examinee, the timer 51 is started by pressing the timer switch 102 (step S2), the barrier filter 42 is inserted by the operation of the fluorescence filter switch 103 (step S3), after which a shutter button (not shown) is pressed to take images.

If it is desired to change the photography mode from this mydriatic fluorescence photography mode to a mydriatic color mode, then the mydriatic color switch 104 is operated; and if it is desired to change the photography mode to the non-mydriatic mode, then the non-mydriatic switch 105 is operated.

If these switches 104 and 105 are pressed during the mydriatic fluorescence photography mode for change to the mydriatic color mode and the non-mydriatic mode, then the timer 51 that was started previously by the timer switch 102 is stopped or reset, and the operation and display of the timer 51 are set to DISABLED/NO (FIG. 2), as discussed earlier. Subsequently, if the mode returns to the mydriatic fluorescence mode by the operation of the mydriatic fluorescence switch 101, then the timer 51 is reset and therefore starts from time zero. By performing control in this manner, unnecessary timing information is neither displayed nor imprinted, and it is also possible to prevent misoperation of the timer 51.

Step S5 to step S8 in FIG. 5 show the control performed to disable the timer, in which, as mentioned above, the timer is not in the timer function hold mode and the photography mode is switched from the mydriatic fluorescence to the normal mydriatic color mode by the mydriatic color switch 104.

Namely, the timer 51 automatically stops in step S6 (stops the timing and resets it to time zero) when the photography mode is switched to the mydriatic color mode by the mydriatic color switch 104 in step S5. The exciter filter 17 and the barrier filter 42 that were previously inserted by the mydriatic fluorescence switch 101 and the fluorescence filter switch 103, respectively, are retracted from the optical path.

Subsequently, when the mode has returned to the mydriatic fluorescence mode by the operation of the mydriatic fluorescence switch 101 (step S7), the operation of the timer 51 is enabled. In this case, the timer 51 was already reset in step S6, so that the timing starts from time zero without error if the timer switch 102 is operated (step S8).

Meanwhile, if it is desired to maintain the function of the timer 51 while performing fluorescence photography, the timer switch 102 is pressed for more than a prescribed time while pressing the fluorescence filter switch 103. In the present embodiment, the timer function hold mode can be set by depressing existing switches 102 and 103, there is no need to modify the hardware and the apparatus can therefore be constituted simply and at low cost.

The operation to hold timer function by the fluorescence filter switch 103 and the timer switch 102 is checked in step S4 and, if no operation for holding the timer function is detected, then control is performed as explained in steps S5 to S8.

The following methods may be adopted as the timer function hold operation in order to enable the timer function hold mode of the present embodiment:

Press the timer switch 102 while pressing the fluorescence filter switch 103 as mentioned above.

Continue pressing the timer switch 102 for a predetermined time.

That is, the timer function can be maintained either by pressing two switches simultaneously or by pressing one switch continuously for a given time.

In this embodiment, (mydriatic) color photography can be performed during the timer function hold mode, and it may be called a "timer function hold mode capable of (mydriatic) color photography interupt".

FIG. 5 describes the operation when the timer function hold operation has been performed in step S4, using as an example a case wherein the mydriatic color switch 104 has been operated, the same as in steps S5 to S8.

Namely, if the timer function hold operation is detected in step S4, then the mode enters the timer function hold mode. At this time, the fact that the timer function hold mode was entered is displayed by changing the display state of the LED 112 (e.g., switching the lamp-on color or to a flashing state). This allows the user to clearly recognize that the timer function hold mode has been entered.

At this point, if the mydriatic color mode is set by the operation of the mydriatic color switch 104 (step S9), then the function of the timer 51 and the display of the timer display unit 111 (or the imprinting to the main optical system, the display on the monitor 40, and the like) continue as described in step S10, unlike step S6.

In step S11, the photography mode returns again to the mydriatic fluorescence mode by the operation of the mydriatic fluorescence switch 101. The timer 51 is not reset, unlike in step S6 and the timer 51 continues the timing that was started when the fluorescent agent was previously injected. Images can thus be taken using this timing information (step S12).

Steps S5 to S8 and steps S9 to S12 in FIG. 5 illustrate, as an example of another photography mode that transitions from the mydriatic fluorescence mode, the mydriatic color mode that transitions by the operation of the mydriatic color switch 104; however, the same control can of course be performed even in the case of the non-mydriatic mode that transitions by the operation of the non-mydriatic switch 105.

By performing the timer function hold operation in the mydriatic fluorescence mode as described in steps S4 and S9 to S12, the timer 51 continues the timing without being reset, even if an operation is performed wherein the photography mode transitions to another mode. Therefore, if the photography mode returns to the mydriatic fluorescence mode by the operation of the mydriatic fluorescence switch 101 after images has been taken in a mode other than the mydriatic fluorescence mode, then it is possible to perform mydriatic fluorescence photography using the timing information of the timer 51 that was previously started.

The following example of control is conceivable when it is desired to stop (cancel) the set timer function hold mode.

First, the mode transitions to the timer function hold mode in the mydriatic fluorescence mode, and the timer function hold mode is cancelled before transitioning to another photography mode (mydriatic color mode or non-mydriatic mode). In this case, the timer switch 102 is once again pressed for at least a fixed time while pressing the fluorescence filter switch 103. This causes the timer function hold mode to be cancelled and the timer to be automatically stopped when the timer switch 102 is pressed or when the photography mode has transitioned to another mode, as is the same as previously discussed (steps S5 to S8).

There is a case where the timer function hold mode is set in the mydriatic fluorescence mode and the photography mode has transitioned to another mode (mydriatic color mode or non-mydriatic mode). If, in this case, the timer function hold mode should be cancelled, then the timer switch 102 is pressed once again. This causes the timer 51 to be stopped. In the non-fluorescence modes such as the mydriatic color mode and the non-mydriatic mode it is preferable that the starting of the timer by the timer switch 102 is disabled, based on the principles in FIG. 2.

On the other hand, the timer function hold mode is set in the mydriatic fluorescence mode, and the photography mode has transitioned to another mode (mydriatic color mode or non-mydriatic mode) and then returned to the mydriatic fluorescence mode. In this case, the timer function hold mode can be cancelled by the normal timer stop operation using the timer switch 102. Furthermore, the timer function hold mode may be canceled and the timer may be stopped when the photography mode has transitioned to another mode. In this case, the setting of the timer function hold mode is effective only for one cycle wherein the photography mode transitions from the mydriatic fluorescence mode to another mode and returns to the mydriatic fluorescence mode, and the timer function hold mode is canceled if the photography mode has transitioned to another mode.

Figure 6:
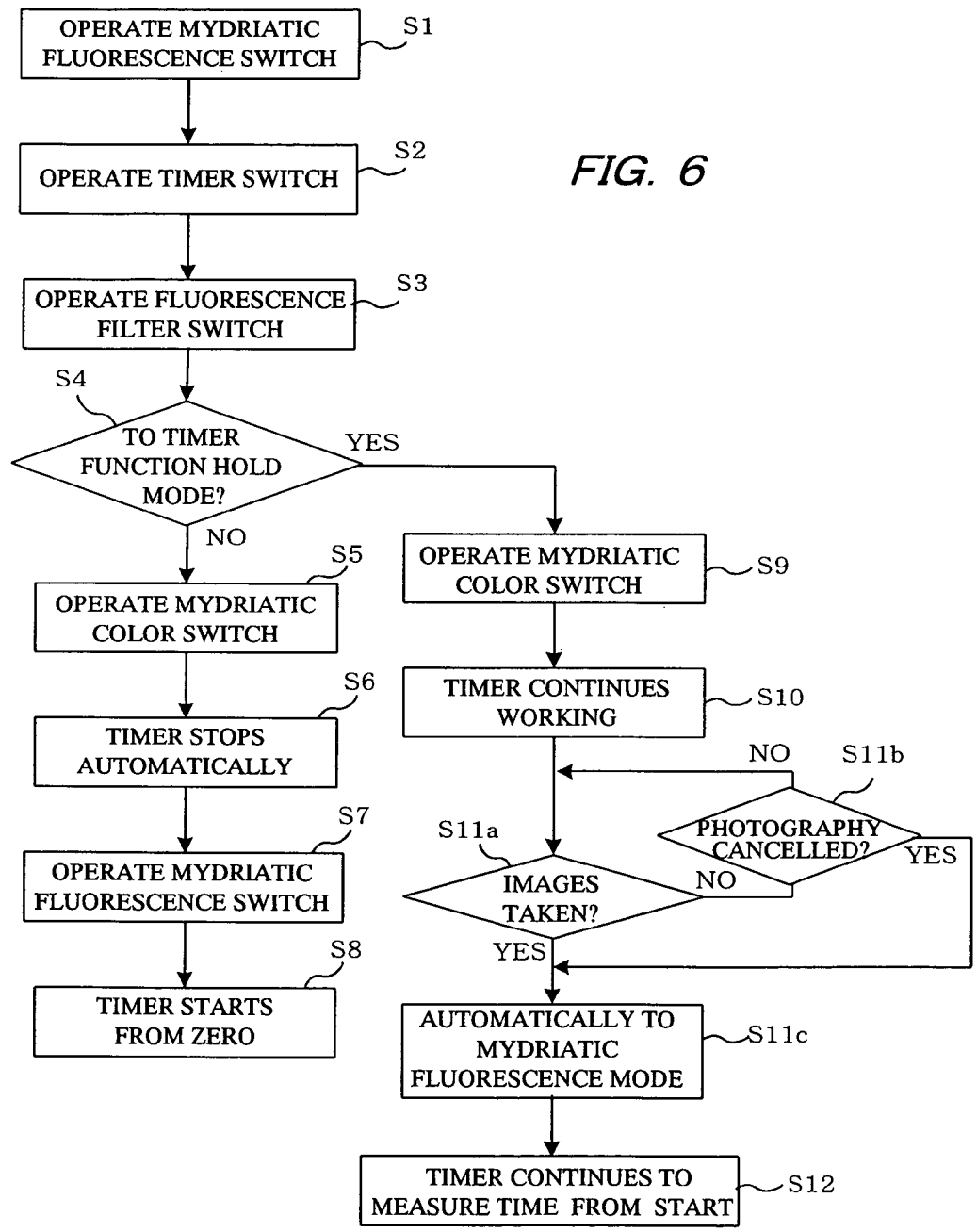
FIG. 6 is a flow chart showing a modification of the flow in FIG. 5.

Step S11 in the flow in FIG. 5 can be modified as shown in steps S11a to S11c in FIG. 6.

After the mydriatic color mode is set in step S9 in FIG. 6, the exciter filter 17 and the barrier filter 42 are retracted from the optical path, and mydriatic color photography is performed. The function of the timer 51 is maintained and the display of the timer display unit 111 (or the imprinting to the main optical system, the display on the monitor 40, and the like) continues unaltered as described in step S10.

At this stage, the user can perform mydriatic color photography by using the shutter button (not shown). The prescribed number of mydriatic color images taken may be determined in advance by default to be one to several images, or can be set in advance by a setting means, which is not shown (e.g., by an unillustrated numeric keypad and the like that is provided to the operation unit 52), and it is determined in step S11a whether this prescribed number of images has been taken.

When it is confirmed that the prescribed number of images has been taken in step S11a, the photography mode automatically returns, to the original mydriatic fluorescence mode in step S11c. At this time, the exciter filter 17 and the barrier filter 42 are reinserted in the optical path.

It is preferable that the mydriatic color photography can be cancelled by a prescribed operation (e.g., once again pressing the timer switch 102 for at least a fixed time while pressing the fluorescence filter switch 103, using another cancel key, and the like). The cancel of mydriatic color photography is detected in step S11b and the flow transitions from step S11b to step S11c. This enables the user to return to the original mydriatic fluorescence mode before the prescribed number of images has been taken.

It is preferable that the timing data of the timer that is displayed on the display apparatus is not recorded (imprinted) on the image taken in the interrupting mydriatic color photography (or also not recorded as imaging data on the HDD and the like). Normally, the timing data of the timer is important in the fluorescence mode and is imprinted on the taken image or recorded as imaging data on the HDD and the like. Since such timing data of the timer is not recorded on the image taken in the mydriatic color photography, it is easier to interpret the image, the imaging data, and the like, and it is also possible to save storage space on the HDD and the like.

In the embodiment in FIG. 5 it is necessary to operate the mydriatic fluorescence switch 101 again in order to return to the mydriatic fluorescence mode. However, in the embodiment in FIG. 6, the photography mode returns automatically to the original mydriatic fluorescence mode upon completion of the preset (or default) prescribed number of images to be taken. This allows the operation procedure of the user to be further simplified and prevents misoperation, such as forgetting to return to the mydriatic fluorescence mode.

Figure 7:
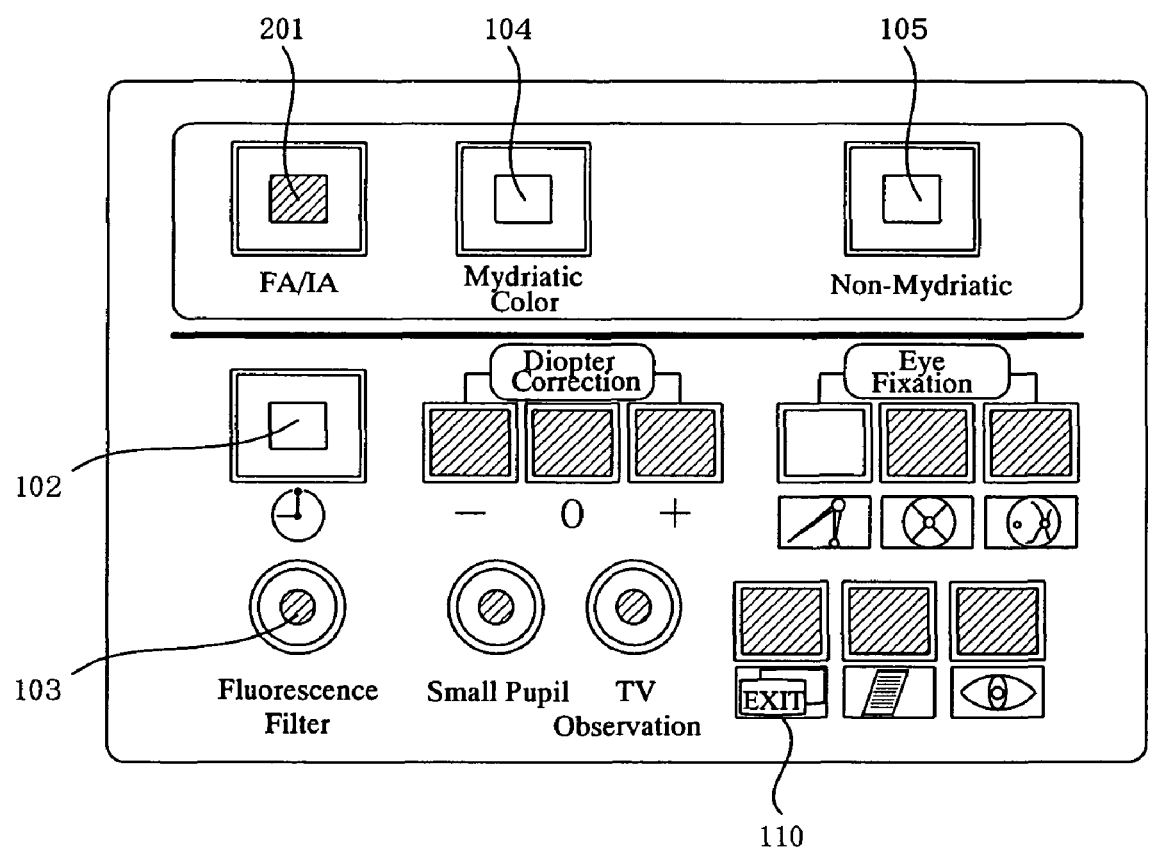
FIG. 7 is an explanatory view showing a different operation panel of the apparatus of FIG. 1.
Figure 8:
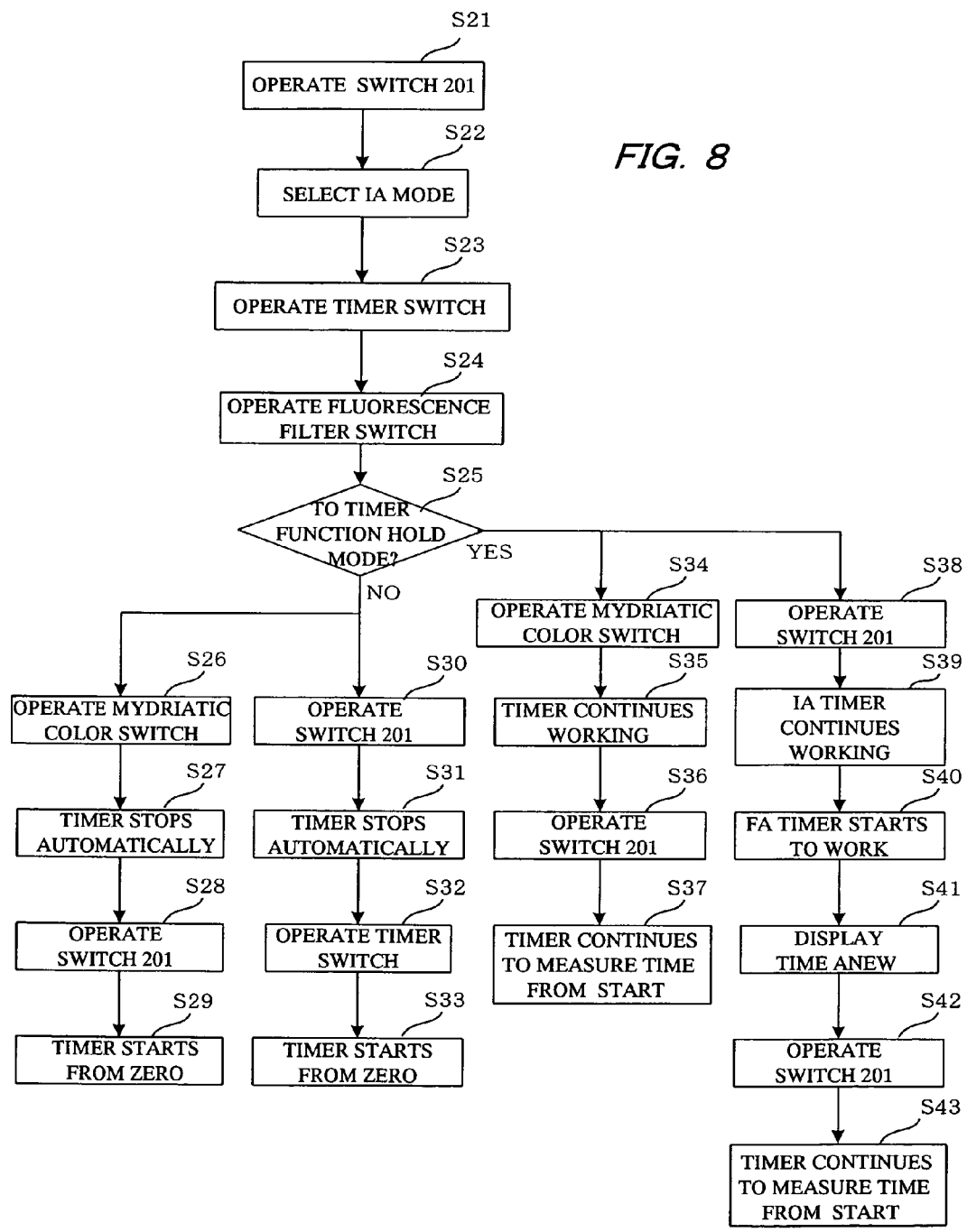
FIG. 8 is a flow chart showing another embodiment of the controls of timers in the photography modes.

FIG. 7 and FIG. 8 show another embodiment in which a user interface (FIG. 7) is used to enable the setting of infrared light-excited fluorescence photography. The constitution of the fundus camera is the same as that shown in FIG. 1 and FIG. 2, and the present embodiment also uses the operation panel of FIG. 3.

FIG. 7 describes an example of a substitute for the operation panel in FIG. 4. FIG. 7 differs from FIG. 4 in that a fluorescence switch 201 is provided instead of the mydriatic fluorescence switch 101; otherwise, the constitution is the same as in FIG. 4 and elements and devices that are identical or equivalent to those in FIG. 4 are assigned the identical symbol.

The fluorescence switch 201 comprises a switch capable of selecting two fluorescence modes, i.e., visible light-excited fluorescence mode (FA mode) and infrared light-excited fluorescence mode (IA mode). The normal operation when performing infrared light-excited fluorescence photography is to press the fluorescence switch 201 in the selected infrared light-excited fluorescence mode. However, the most convenient fluorescence mode selection system is to use the toggle action of the fluorescence switch 201, wherein the mode toggles between the visible light-excited fluorescence mode and the infrared light-excited fluorescence mode for each depressing of the switch.

Of course, if the photography mode has transitioned to visible light-excited fluorescence (FA) by the operation of the fluorescence switch 201, the visible light-excited fluorescence exciter filter 17 is inserted in the optical path and, if the photography mode has transitioned to infrared light-excited fluorescence (IA), then the infrared light-excited fluorescence exciter filter 18 is inserted into the optical path.

In addition, a second timer 55 as shown in FIG. 1 is used in the present embodiment. The timer 51 and the timer 55 are used so that they independently measure the elapsed time for the infrared light-excited fluorescence mode and the visible light-excited fluorescence mode, respectively.

FIG. 8 shows the control performed in the present embodiment in a format the same as in FIG. 5. The controlling means in FIG. 8 is stored in advance in the ROM 54 as a control program of the control unit 39. FIG. 8 describes how control is performed depending upon the presence of the timer function hold mode, i.e., function in the case wherein the photography mode first transitions to the infrared light-excited fluorescence mode, and then enters, as another (non-fluorescence) mode, the mydriatic color mode by the operation of the mydriatic color switch 104 (steps S26 to S29 or steps S34 to S37), and function for the case wherein the fluorescence switch 201 is pressed once again and the photography mode enters, as another fluorescence mode, the visible light-excited fluorescence mode (steps S30 to S33 and steps S38 to S43). FIG. 8 does not show the non-mydriatic mode as another (non-fluorescence) mode, the same as in FIG. 5, but the function thereof is equivalent to the function for the case wherein the photography mode has entered the mydriatic color mode (steps S26 to S29 or steps S34 to S37).

The fluorescence switch 201 is operated in steps S21 and S22 to perform infrared light-excited fluorescence photography and transfer the photography mode to the infrared light-excited fluorescence mode (IA mode). Then, a fluorescent agent is intravenously injected, and the timer switch 102 is pressed to start the timer 51 (step S23). If the barrier filter 43 for infrared light-excited fluorescence is inserted by the operation of the fluorescence filter switch 103 (step S24), then images can be taken by the operation of a shutter button (not shown) in this state.

The timer function hold mode is set by pressing the timer switch 102 for at least a fixed time while pressing the fluorescence filter switch 103, the same as in FIG. 5.

This timer function hold operation is detected in step S25, and control switches between control of the timer function hold mode described in steps S34 to S43 and control of the normal mode (non-timer function hold mode) described in steps S26 to S33. The same as in FIG. 5, the user is informed by the display of the LED 112 whether the timing mode is in the timer function hold mode or in the normal mode (non-timer function hold mode).

If the normal mode (non-timer function hold mode) is set in the infrared light-excited fluorescence mode in steps S21 to S24, then the timer 51 is automatically stopped (timing is stopped and reset to time zero) in step S27 if the photography mode is switched to another mode, e.g., if switched to the (non-fluorescence) mydriatic color mode by the operation of the mydriatic color switch 104 (step S26). At this time, the exciter filter 18 and barrier filter 43, which were previously inserted respectively, are retracted from the optical path.

The photography mode returns again to the infrared light-excited fluorescence mode by the operation of the fluorescence switch 201 (step S28), and the operation of the timer 51 is made effective. In this case, the timer switch 102 can be operated to start timing from time zero without error (step S29) because the timer was already reset in step S27.

On the other hand, if the normal mode (non-timer function hold mode) is set (step S25) in a state wherein the photography mode is in the infrared light-excited fluorescence mode as in steps S21 to S24, then the timer 51 automatically stops (timing stops and is reset to time zero) in step S31 if the photography mode transitions to another fluorescence mode, i.e., the visible light-excited fluorescence mode, by the operation of the fluorescence switch 201 (step S30). At this time, the infrared exciter filter 18 and barrier filter 43, which were previously inserted by the mydriatic fluorescence switch 101 and the fluorescence filter switch 103 respectively, are retracted from the optical path, and the visible light exciter filter 17 and barrier filter 42 are inserted in the optical path instead. Because the timer operation is enabled in the visible light-excited fluorescence mode (FIG. 2), the timer 51 is started from time zero in this case (step S33) if the timer switch 102 is operated (step S32).

However, if the timer function hold mode is set (step S25) by a previous timer function hold operation in a state wherein the photography mode is in the infrared light-excited fluorescence mode, as in steps S21 to S24, and if the photography mode switches to another mode, e.g., to the (non-fluorescence) mydriatic color mode, by the operation of the mydriatic color switch 104 (step S34), then the function of the timer 51, the display and imprinting of the timing information by the timer display unit 111, and the like, are continued (step S35).

If the photography mode returns to the infrared light-excited fluorescence mode by the operation of the fluorescence switch 201 (step S36), then the timer 51 is not reset, unlike in step S27, and therefore counts the elapse time in step S37 by continuing the timing that was started when the fluorescent agent was injected, and images can be taken using this timing information.

On the other hand, when the timer function hold mode is set (step S25) in a state wherein the photography mode is in the infrared light-excited fluorescence mode as in steps S21 to S24, and the photography mode enters another fluorescence mode, i.e., the visible light-excited fluorescence mode, by the operation of the fluorescence switch 201 (step S38), the timer 51, which is used as the infrared light-excited fluorescence timer (IA timer), continues to function (step S39).

Furthermore, control is performed so that the timer 55, which is used as the visible light-excited fluorescence timer (FA timer), can be started separately (step S40) by the operation of the timer switch 102. Then, the timing information of the timer 55 is newly displayed on the timer display unit 111 (or imprinted) (step S41). Thus, it is possible to perform photography using the timer 55 as an independent visible light-excited fluorescence timer in the visible light-excited fluorescence mode.

If the photography mode returns to the infrared light-excited fluorescence mode by the operation of the fluorescence switch 201 (step S42), then the display (or imprinting) of the timer display unit 111 switches to the timing information of the timer 51 because the timing thereof is continuing. Thereby, images can be taken in the infrared light-excited fluorescence mode by continuing to use the timing information of the timer 51 (step S43), which was initially started, for example, when the fluorescent agent was intravenously injected.

FIG. 8 shows the function for the case wherein the infrared light-excited fluorescence mode is selected by the operation of the fluorescence switch 201, but of course the same control may be performed for the case wherein the visible light-excited fluorescence mode is selected by the operation of the fluorescence switch 201. In that case, the above explanation is valid if the timer 51 that continues in step S39 is read as timer 55, and the timer 55 that is newly started in steps S40 and S41 is read as timer 51.

It is also preferable that the operation from the cancellation of the timer function hold mode to the stopping of the timer can be performed by the same operation, as discussed at the conclusion of the embodiment in FIG. 5.

In above described two embodiments in FIGS. 5 and 8, it is possible to enable the timer function hold mode by a specific operation (in the above example, the timer switch 102 is pressed for at least a fixed time while pressing the fluorescence filter switch 103, but a person of skill in the art may adopt another operation method). If this timer function hold mode is enabled, a timer that was started in a certain photography mode can be made to continue its function even after the photography mode has subsequently transitioned to another photography mode, and photography can be continued using the initially started timing information when the mode returns to the original mode.

In addition, the LED 112 clearly displays whether the timing mode is in the timer function hold mode or the normal mode (non-timer function hold mode), and it is consequently possible for the user (examiner) to reliably recognize whether the timer that was previously started is continuing to run, and to prevent misoperation.

Of course, if the timer function hold mode was not set, then the timer is automatically stopped and reset when a mode switching occurs, as in the conventional case, and it is consequently possible to prevent misoperation, such as forgetting to turn off the timer.

Furthermore, even if timers for visible light-excited fluorescence and infrared light-excited fluorescence modes are provided as in FIG. 8, it is possible to use those timers to maintain the timing of the timer used for the initially selected fluorescence mode; in that case, there is no risk that the operation will become complicated because the timer function hold operation is the identical operation.

Figure 9:
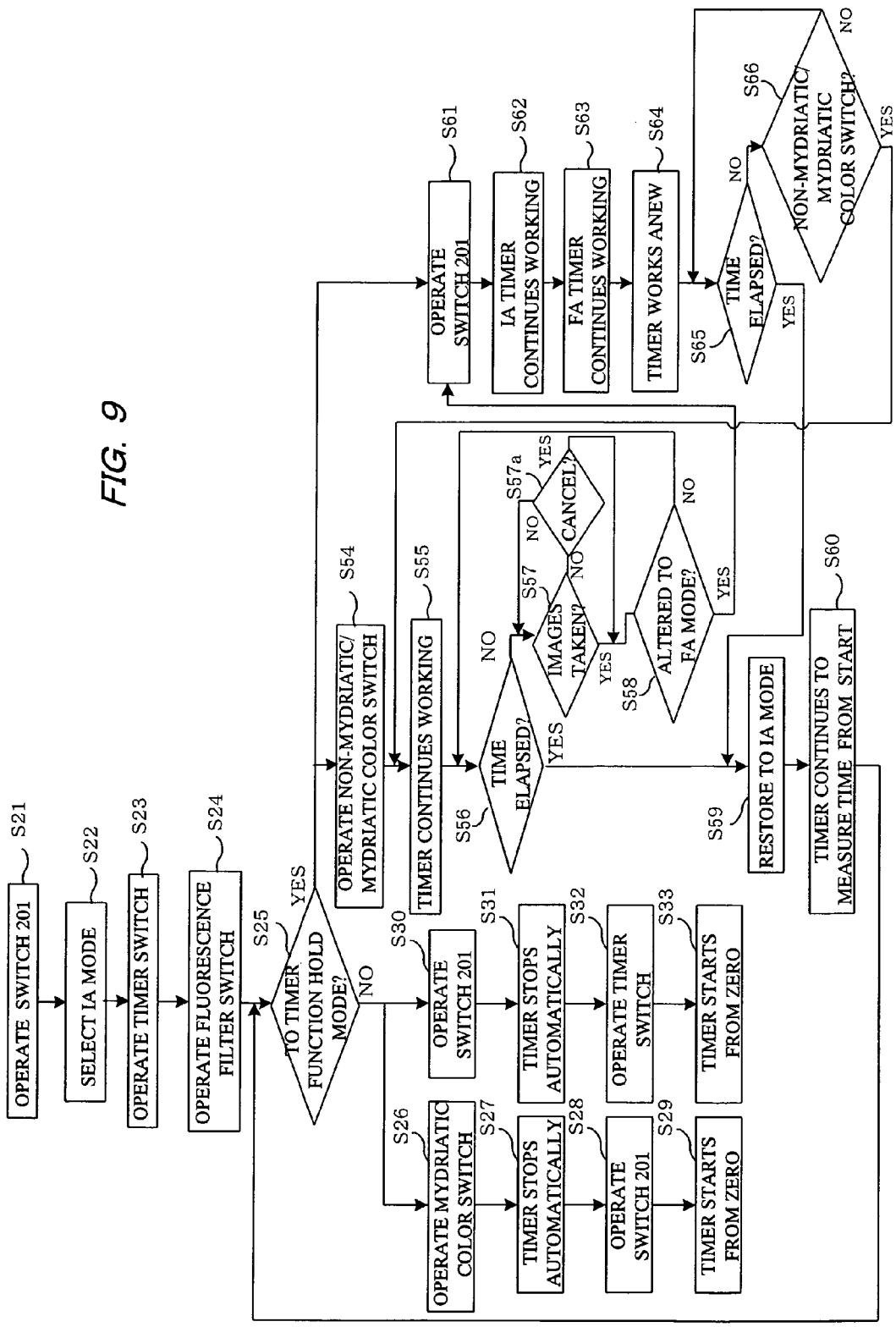
FIG. 9 is a flow chart showing still another embodiment of the controls of timers in the photography modes.

FIG. 9 shows another embodiment of the present invention. The controlling means in FIG. 9 is stored in advance in the ROM 54 as a control program of the control unit 39.

The processes in steps S21 to S33 in FIG. 9 are the same as those in FIG. 8, so that their detailed explanation will be omitted.

When, in FIG. 9, the timer function hold mode is set (step S25) and the photography mode switches to another one, e.g., to the (non-fluorescence) mydriatic color mode by the operation of the mydriatic color switch 104 as in step S54 (or to the non-mydriatic mode by the operation of the non-mydriatic switch 105), the exciter filter 17 and the barrier filter 42, which were previously inserted by the operation of the mydriatic fluorescence switch 101 and the fluorescence filter switch 103 respectively, are retracted from the optical path, and mydriatic color images (or non-mydriatic images) can be taken while continuing unaltered the function of the timer 51, the display and imprinting of the timing information by the timer display unit 111, and the like (step S55).

The period of time (step S57 and step S57a) when this mydriatic color photography (or non-mydriatic photography) can be performed is interposed between the determinations of step S56 and step S58 in FIG. 9.

Step S56 determines whether a prescribed time for returning to the infrared light-excited fluorescence photography (e.g., the time until the latter stage of the infrared light-excited fluorescence photography) has elapsed, and step S58 determines whether a transition to the visible light-excited fluorescence photography mode (set by the operation of the fluorescence switch 201) has been set.

The user can perform the interrupt photography using the shutter button (not shown) while the determinations of step S56 and step S58 are not YES.

The apparatus can be constituted so that the prescribed number of images to be taken in this interrupt photography is determined by default to be from one to on the order of several images, or can be set beforehand by an unillustrated setting means (such as an unillustrated numeric keypad provided on the operation unit 52). It is determined in step S57 whether this prescribed number of images has been taken. In step S57*a*, it is also determined whether the operation that stops the running photography (depressing of a prescribed singular key or a combination of a plurality of keys) has been performed.

The apparatus may be constituted so that the timing data of the timer that is displayed on the display apparatus is not recorded (imprinted) on the image taken by this photography (or not recorded as imaging data on the HDD and the like), the same as in FIG. 6.

If it is confirmed in step S57 that the prescribed number of images has been taken, and if it has been further confirmed in step S58 that the photography mode was not switched to visible light-excited fluorescence photography and confirmed in step S56 that the prescribed time for returning to the infrared light-excited fluorescence photography has elapsed, then the photography mode automatically returns to the original infrared light-excited fluorescence mode in step S59. At this time, the exciter filter 18 and the barrier filter 43 are reinserted in the optical path. Thus, unlike FIG. 8, there is no need to perform the operation of returning to the infrared light-excited fluorescence mode by the operation of the fluorescence switch 201.

Because the timer 51 is not reset unlike in step S27, the timer 51 in step S60 continues to count the timing that was started when the fluorescent agent was intravenously injected, and infrared light-excited fluorescence photography can be performed using this timing information.

If the photography mode enters another fluorescence mode, i.e., the visible light-excited fluorescence mode, by the operation of the fluorescence switch 201 (step S61) in the timer function hold mode, then the timer 51, which is used as the infrared light-excited fluorescence timer, continues to function (step S62).

At this time, the timer 55, which is used as the visible light-excited fluorescence timer, can be started separately (step S63) and, if the timer switch 102 is operated, then the timing information of the timer 55 is newly displayed on the timer display unit 111 (or imprinted by the main optical system) (step S64). Thus, it is possible to perform photography using the timer 55 as an independent visible light-excited fluorescence timer in the visible light-excited fluorescence mode.

The elapse of the prescribed time (e.g., the time until the preset timing of the latter stage infrared light-excited fluorescence photography) is also set as a condition (step S65) for the return from the function of the interrupting visible light-excited fluorescence mode to the infrared light-excited fluorescence mode, and the method transitions from step S65 to step S59 if this prescribed time elapses.

Because the timing by the timer 51 continues in the infrared light-excited fluorescence mode, which is the mode to which the photography mode has returned, the display (or imprinting) of the timer display unit 111 switches to the timing information of the timer 51. Thus, images can be taken in the infrared light-excited fluorescence mode by continuing to use the timing information of the timer 51, which was initially started, for example, when the fluorescent agent was intravenously injected.

If the operation of switching to the (non-fluorescence) mydriatic color mode by the operation of the mydriatic color switch 104 (or the operation of switching to the non-mydriatic mode by the operation of the non-mydriatic switch 105) is detected in step S66 within the elapse of the prescribed time (step S65), then the method transitions to step S55.

Figure 10:
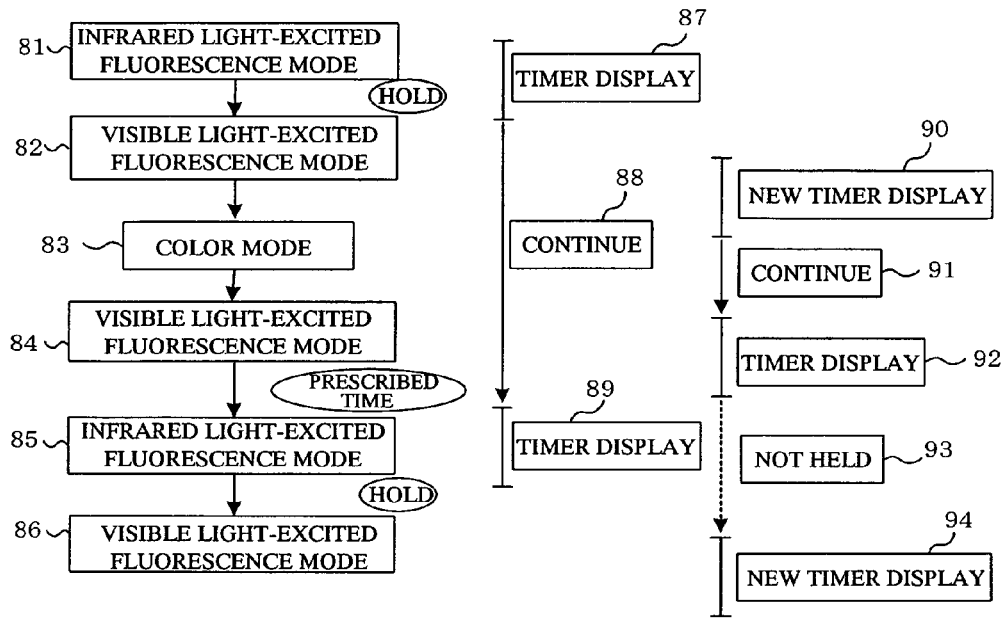
FIG. 10 is an explanatory diagram showing one example of a photography sequence implemented in the present invention.

FIG. 10 shows one example of the operation implemented by the control in FIG. 9 (or FIG. 10 as well). The example on the left side of FIG. 10 shows the transition to the mode selected by the user, the example in the center the timing of the infrared light-excited fluorescence timer, and the example on the right the timing of the visible light-excited fluorescence timer.

In FIG. 10, the infrared light-excited fluorescence mode is first selected (81). If it is determined that the timer function hold mode is set (step S25 in FIG. 9), the function of the infrared light-excited fluorescence timer continues (is maintained), as shown in the center part of FIG. 10, even if another mode is selected midway (82, 83, 84). At this time, the infrared light-excited fluorescence timer is displayed (87, 89) while the infrared light-excited fluorescence mode is selected, and the function of the infrared light-excited fluorescence timer continues (88, as well as steps S60 and S62 in FIG. 9) while another mode is selected (82, 83, 84).

In FIG. 10, the photography mode switches from the infrared light-excited fluorescence mode to the visible light-excited fluorescence mode (82), the color mode (83), and once again to the visible light-excited fluorescence mode (84); however, if the visible light-excited fluorescence mode is selected (82), then the visible light-excited fluorescence timer is activated (90, and step S64 in FIG. 9) and the function thereof is maintained (91).

Namely, the visible light-excited fluorescence timer is displayed (90, 92) while the visible light-excited fluorescence mode is selected (82, 84), and the function of the visible light-excited fluorescence timer is maintained (91) for the period of time of the inserted color mode (83).

The visible light-excited fluorescence timer is not displayed in the selected color mode (83) while in the visible light-excited fluorescence mode (82, 84).

Furthermore, in FIG. 10, the photography mode automatically returns to the infrared light-excited fluorescence mode (85, and step S56 in FIG. 9) based on the timing of the initially activated infrared light-excited fluorescence timer. At this time, the function of the fluorescence timer is automatically stopped (93). In the infrared light-excited fluorescence mode, which is the mode to which the photography mode is automatically returned, the timing information of the infrared light-excited fluorescence timer, which was initially activated and maintained, is displayed (89).

Assume in FIG. 9 that another examinee is subsequently examined; in this case, the method transitions from step S103 to step S101 in FIG. 11, as discussed above, in accordance with a prescribed operation (e.g., operation of the EXIT switch 110), and the mode settings up to that point, including the timer hold mode, are canceled in step S101. Furthermore, in the photographing process (step S102 in FIG. 11), a new visible light-excited fluorescence mode is selected (86), and a new fluorescence timer is activated (94) in that case. In this visible light-excited fluorescence mode, it is likewise possible to perform the timer function hold operation, the same as mentioned above.

Furthermore, FIG. 9 explains the function for the case wherein the infrared light-excited fluorescence mode is selected by the operation of the fluorescence switch 201, but of course the same control may be performed for the case wherein the visible light-excited fluorescence mode is selected by the operation of the fluorescence switch 201. In that case, the above explanation is valid if the timer 51 that continues in step S59 is read as timer 55, and the timer 55 that is newly started in steps S60, S61 is read as timer 51.

The present invention can be applied to various ophthalmic photographic apparatuses that perform ophthalmic photography using a timer, and more particularly to various ophthalmic photographic apparatuses wherein the timing information of a timer plays an important role, such as in the fluorescence photography mode.

What is claimed is:

1. An ophthalmic photographic apparatus having a plurality of photography modes and a timing means for measuring the elapsed time since its start by the command of a user, comprising:

timer function holding means responsive to a prescribed timer function hold operation in a first photography mode for setting a timer function hold mode;

wherein, when the timer function hold mode is set in the first photography mode, the timing means continues measuring the time even after the first photography mode is switched therefrom to a second photography mode, and the first photography mode is restored automatically after a prescribed number of images is taken in the second photography mode or after a prescribed time is elapsed after the first photography mode is switched to the second photography mode.

2. An ophthalmic photographic apparatus according to claim 1; wherein the first photography mode is a fluorescence photography mode.

3. An ophthalmic photographic apparatus according to claim 1; wherein the first photography mode is an infrared light-excited fluorescence photography mode.

4. An ophthalmic photographic apparatus according to claim 1; wherein after the first photography mode is switched to the second photography mode, the timing information of the timing means is neither displayed, nor recorded.

* * * * *